United States Patent
Browne

(10) Patent No.: US 6,706,094 B2
(45) Date of Patent: Mar. 16, 2004

(54) COLLECTION OF DISSOLVED GASES FROM GROUNDWATER

(75) Inventor: Bryant Alan Browne, Stevens Point, WI (US)

(73) Assignee: WiSys Technology Foundation Inc., Madison, WI (US)

(*) Notice: Subject to any disclaimer, the term of this patent is extended or adjusted under 35 U.S.C. 154(b) by 108 days.

(21) Appl. No.: 10/144,606

(22) Filed: May 13, 2002

(65) Prior Publication Data

US 2003/0209144 A1 Nov. 13, 2003

(51) Int. Cl.⁷ ................................................ B01D 19/00
(52) U.S. Cl. ..................... 95/241; 73/61.41; 73/863.21; 95/254; 95/260; 96/155; 96/194; 96/204; 96/413
(58) Field of Search .......................... 95/241, 252, 254, 95/266, 260, 262, 248; 96/155, 193, 194, 204, 206, 220, 413; 210/180; 73/61.41, 152.23, 863.21

(56) References Cited

U.S. PATENT DOCUMENTS

| | | | |
|---|---|---|---|
| 3,255,575 A | * | 6/1966 | Roberts |
| 3,303,002 A | * | 2/1967 | McAuliffe |
| 3,347,096 A | * | 10/1967 | Person |
| 3,455,144 A | * | 7/1969 | Bradley |
| 3,885,930 A | * | 5/1975 | Scherrer |
| 3,957,439 A | * | 5/1976 | Prescott |
| 4,022,592 A | * | 5/1977 | Saaski |
| 4,216,089 A | | 8/1980 | Boon et al. |
| 4,522,218 A | * | 6/1985 | Konak |
| 4,548,622 A | | 10/1985 | Suzuki et al. |
| 4,764,344 A | | 8/1988 | Knab |
| 4,862,729 A | | 9/1989 | Toda et al. |
| 5,103,578 A | | 4/1992 | Rickard |
| 5,250,104 A | * | 10/1993 | Berger et al. |
| 5,329,811 A | | 7/1994 | Schultz et al. |
| 5,340,384 A | | 8/1994 | Sims |
| 5,442,948 A | | 8/1995 | Cowing |
| 5,509,294 A | | 4/1996 | Gowing |
| 5,632,603 A | * | 5/1997 | Taylor et al. |
| 5,993,515 A | | 11/1999 | Sirkar |
| 6,082,174 A | | 7/2000 | Lee et al. |

OTHER PUBLICATIONS

Busenberg, Eurybiades and Plummer, L. Niel, (2000), Dating young groundwater with sulfur hexafluoride: Natural and anthropogenic sources of sulfur hexafluoride, *Water Resources Research*, vol. 36, No. 10, pp. 3011–3030.

Busenberg, Eurybiades and Plummer, L. Niel, (1992), Use of Chlorofluorocarbons ($CCl_3F$ and $CCl_2F_2$) as Hydrologic Tracers and Age–Dating Tools: the Alluvium and Terrace System of Central Oklahoma, *Water Resources Research*, vol. 28, No. 9, pp. 2257–2283.

* cited by examiner

*Primary Examiner*—Duane S. Smith
(74) *Attorney, Agent, or Firm*—Craig A. Fieschko, Esq.; DeWitt Ross & Stevens S.C.

(57) ABSTRACT

A system for rapid collection of large volumes of dissolved gases from groundwater pumps the water from a large-diameter passage through a small-diameter restrictor passage, and then into a flow-through collection chamber. The small-diameter passage causes a drop in the hydrostatic pressure of the groundwater traveling therein, causing spontaneous ebullition of gas bubbles which are then collected in the collection chamber. Testing reveals that the gases are collected in proportion to their presence in the groundwater, and thus the system allows accurate quantification of concentrations of dissolved gas in groundwater. The system may beneficially be made easily portable, thereby allowing its use in the field as well as in laboratory settings.

20 Claims, 1 Drawing Sheet

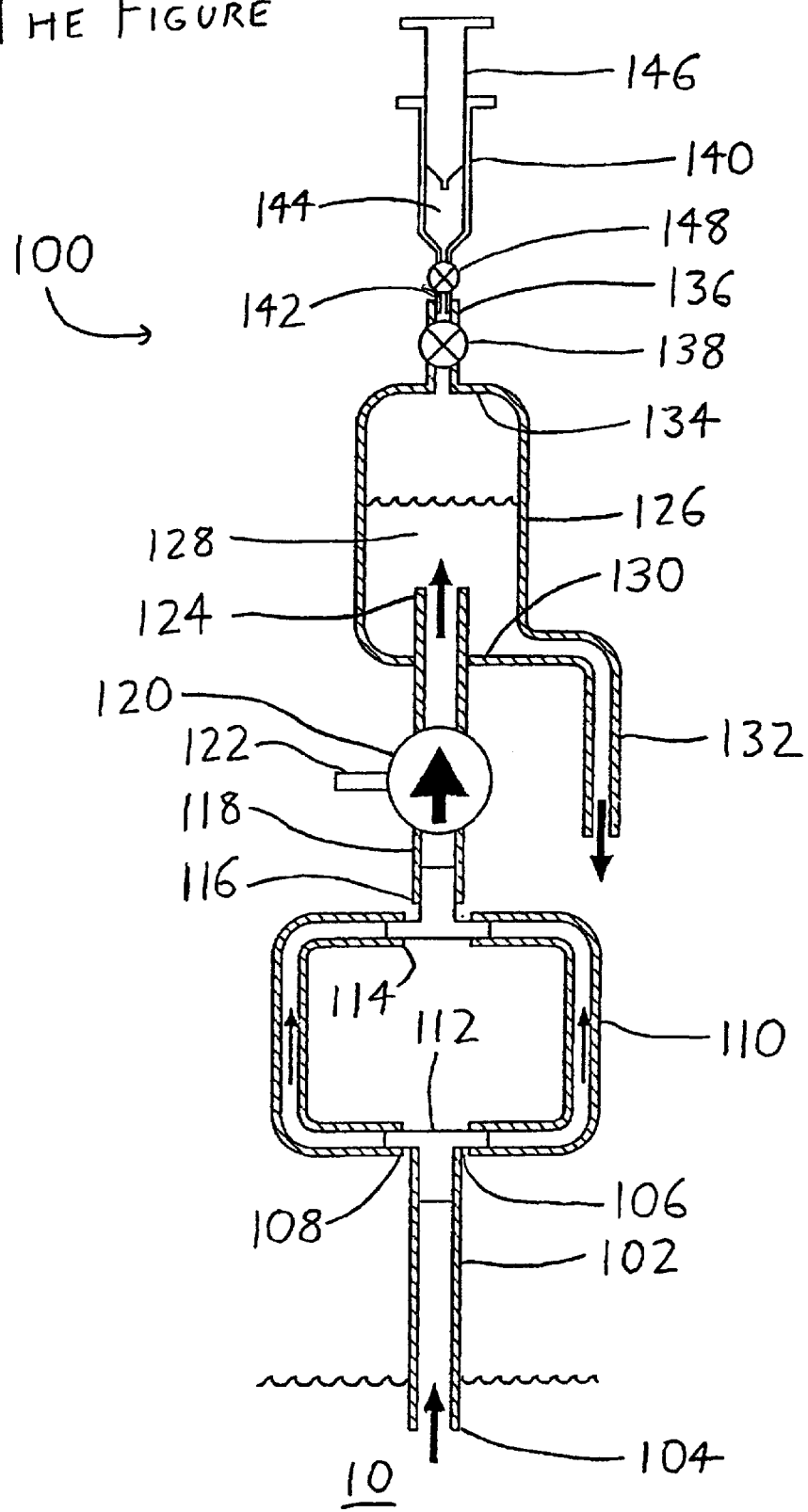
The Figure

COLLECTION OF DISSOLVED GASES FROM GROUNDWATER

FIELD OF THE INVENTION

This disclosure concerns an invention relating generally to methods and apparata for collecting and analyzing gases dissolved within liquids, and more specifically to the collection and analysis of dissolved gas within groundwater.

BACKGROUND OF THE INVENTION

Groundwater, i.e., subsurface waters such as aquifers, wells, etc. and surface waters such as lakes, streams, etc., is a frequent subject of environmental and biogeochemical study. Often, the characteristics and behavior of the groundwater can be at least partially determined by studying gases dissolved within the groundwater. As examples, dissolved gases are often used to generate estimates of denitrification from excess $N_2$ (1, 2) (these numbers referring to listed documents set forth in a bibliography elsewhere in this document); to study greenhouse gases in groundwater (3,4); to evaluate terminal electron accepting processes using $H_2$ (5); and to study the cycling of biogeochemically important trace gases such as $CO_2$, $CH_4$, and $N_2O$. Additionally, groundwater studies often utilize dissolved gases as "tracers" which allow tracking of environmental processes, with applications including paleothermometry (6), age-dating (7, 8), estimating groundwater recharge temperature (9), measuring advection and dispersion in rivers and stream (10), tracing of ocean mixing and circulation paths (11), and tracking of volatile pollutants in groundwater (12), among other applications.

However, the measurement of dissolved gases can be a major analytical challenge. For example, when atmospheric gas concentrations are abundant relative to the dissolved gas concentrations, contamination during sampling and analysis is a major concern. Losses during handling and storage can also be a major problem for some gases due to their volatility and/or biodegradability. In addition, for gases that are typically present at very small concentrations (e.g., $SF_6$ and noble gas isotopes), simply attaining a large enough sample to generate a measurable signal can be a major hurdle.

In view of the foregoing difficulties and the importance of obtaining accurate dissolved gas measurements, a wide variety of sampling and storage procedures have evolved for dissolved gases. Groundwater sampling methods include collection of water in sealed bottles (with or without chemical preservation) for equilibration of gases in the headspace above the water sample (3,4,13); flame sealing of water samples in glass ampules under high purity gases to protect the sample from contamination with the atmosphere (8); collection in copper tubes with stainless steel pinch-offs (14); bubble stripping, diffusion probes, and downhole samplers (15); and others. Complex devices and methods may also be required to extract the gases from the groundwater and to introduce and process gas samples within an analytical instrument. These include, for example, purge and trap devices for analysis of VOCs, trace gases, CECs and $SF_6$ (7 and 8), and highly refined vacuum extraction devices in-line with analytical instruments (14).

The foregoing devices and methods for groundwater sampling and dissolved gas collection suffer from the problems that they can be time-consuming, expensive, and difficult to operate (particularly in field conditions). Thus, it would be useful to have available further devices and methods for groundwater sampling and dissolved gas collection and analysis which at least partially overcome some of these difficulties.

SUMMARY OF THE INVENTION

The invention involves methods and apparata for dissolved gas collection which are intended to at least partially solve the aforementioned problems. To give the reader a basic understanding of some of the advantageous features of the invention, following is a brief summary of preferred versions of the collection devices and methods. As this is merely a summary, it should be understood that more details regarding the preferred versions may be found in the Detailed Description set forth elsewhere in this document. The claims set forth at the end of this document then define the various versions of the invention in which exclusive rights are secured.

An apparatus for collecting dissolved gases from groundwater is provided wherein the groundwater of interest for study is supplied to an intake line having an inlet end and a downstream outlet end. One or more restrictor lines are then provided downstream from the outlet end of the intake line, with the restrictor lines promoting a hydrostatic pressure drop in the groundwater traveling therein. This pressure drop can be generated owing to pumping forces working against resistance (i.e., frictional losses) from the restrictor lines, which resistance may be enhanced by decreasing the flow area of each restrictor line (i.e., the area of the flow passage measured perpendicular to the direction of flow) and/or increasing the length of each restrictor line. Alternatively or additionally, a pressure drop can be generated or enhanced by having the combined flow areas of the restrictor lines be less than the flow area of the intake line, whereby the fluid velocity of the groundwater is increased to generate a corresponding pressure drop. When the groundwater is supplied from the intake line and its pressure is decreased within the restrictor lines, the dissolved gases (if any) within the groundwater will precipitate from the groundwater. Thus, the dissolved gases begin to bubble from the groundwater flowing within the restrictor lines.

A gas collection chamber is then situated downstream from the restrictor line(s), with the gas collection chamber having an interior wherein the precipitated gas bubbles may collect near its upper side. Thus, as the flow of groundwater continues, the amount of collected gas at the upper side of the gas collection chamber grows. A disposal line then exits the gas collection chamber, preferably near the lower side of its interior and below the level at which the groundwater from the restrictor lines enters the gas collection chamber, so that degassed groundwater will flow from the disposal line but the collected gases remain within the gas collection chamber.

If the source of the groundwater is not pressurized such that it will flow through the lines of the apparatus of its own accord (as where the groundwater is supplied from an artesian well), a pump may be situated somewhere among or between the foregoing components to induce flow. A preferred arrangement is to situate any pump downstream from the restrictor lines so that the pressure drop within the restrictor lines (and thus the precipitation of any gases from the groundwater within the restrictor lines) is enhanced by the pump suction.

To remove at least a portion of the collected gases from the gas collection chamber, a sampling port is preferably provided at or near the upper side of the interior of the gas collection chamber where the precipitated gases collect. The sampling port preferably bears a valve, and is adapted for removable attachment of a sample collector (such as a syringe) having an adjustable interior volume. Thus, the valve may be opened and the collected gases may be drawn off into the sample collector to be provided to a suitable analysis device. The collected gases may then be analyzed by gas chromatography or other methods to determine their contents. Alternatively, analytical instrumentation for gas analysis can be directly connected to the sampling port so that analysis can occur concurrently with collection of gases.

Conveniently, the foregoing apparatus may be provided in a portable and easily disassembled and reassembled form so that it may be easily used in the field as well as in a laboratory. As an example, the intake and restrictor lines may be provided by easily folded flexible plastic tubing, and the collection chamber (which is preferably formed of rigid plastic or glass) can be sized so that it may be easily held by one hand. The pump (if present) may take the form of a laboratory peristaltic (or other) pump which has a protruding input shaft adapted for receiving a rotary input from a cordless drill or other easily portable source of a rotary power input. Some of all of the foregoing components may be transparent, allowing the color and particulate content of the sampled groundwater to be observed during gas collection, and allowing any areas of actual or potential fouling to be observed during gas collection.

The invention offers several advantages for gas collection and analysis applications. Initially, it allows multiple sample collection procedures to be combined into one simple method. To illustrate, traditional sampling techniques might require (a) that water samples to be analyzed for CFCs be flame-sealed in glass ampules under high purity $N_2$, with subsequent analysis by purge and cryogenic trap (8), (b) that water samples to be analyzed for $SF_6$ be collected in a 1-liter or larger bottle with a special cap, with subsequent analysis by purge and cryogenic trap (7), (c) that water samples to be analyzed for Ar, $N_2$, and $O_2$ (which is unstable during storage) be collected in a 50-ml septum-sealed glass bottle, with subsequent analysis by a headspace method (13), (d) that water samples to be analyzed for $H_2$ be run through a bubble gas stripping chamber to collect $H_2$, with subsequent analysis by direct injection (15), and (e) that water to be analyzed for $CH_4$ and $N_2O$ be injected into a He or Ar flushed septum-sealed glass bottle, with subsequent analysis of the $CH_4$ and $N_2O$ in the He or Ar headspace (13,3).

In contrast, by use of the invention, one only need collect one or more samples of the collected gas in the field or elsewhere, using a syringe or other sample collector, for later direct injection into a gas chromatograph in the laboratory (though purge and trap and/or other methods may be used if desired). Alternatively, the collected gases can be continuously supplied to analytical instrumentation concurrently with their collection.

Further, the invention avoids the consumption and production of biogenic gases that may occur during storage of a water sample for later analysis. Biotransformation of gases such as $CO_2$, $O_2$, $CH_4$ and $N_2O$ during storage of water samples causes over- or underestimation of the in situ concentration of such gases. Since the invention separates the gases from the water when the water is sampled, only the gas need be stored, thus avoiding aqueous biotransformations during storage.

Additionally, the invention allows the collected gases to be directly supplied to or injected into analytical instrumentation. More elaborate sample introduction and processing approaches (e.g., the valving required to purge and trap CFCs and $SF_6$ from water samples) may be unnecessary depending on the application in question.

Further advantages, features, and objects of the invention will be apparent from the following detailed description of the invention in conjunction with the associated drawings.

BRIEF DESCRIPTION OF THE DRAWINGS

THE FIGURE depicts a simplified diagram of an exemplary version of the apparatus of the invention.

DETAILED DESCRIPTION OF PREFERRED VERSIONS OF THE INVENTION

The FIGURE illustrates an exemplary version of the apparatus of the invention at 100. An intake line 102 has its inlet end 104 situated within a source of groundwater 10, and its outlet end 106 is connected in fluid communication with the inlet ends 108 of a pair of restrictor lines 110 via a T-connector 112. (It should be understood that the intake line 102, the restrictor lines 110, and other components are not shown to scale in the FIGURE, nor are they proportionately illustrated, and in reality they will generally have significantly greater length than the apparent length depicted in the FIGURE.) The outlet ends 114 of the restrictor lines 110 are similarly connected in fluid communication with the inlet end 116 of an output line 118. A pump 120 is situated in the output line 118 to provide the driving force for supplying the groundwater through the apparatus 100, and the pump 120 is preferably provided in a portable form with a protruding input shaft 122 which is adapted for removable attachment to a separate driver (such as a cordless drill) which can supply a rotary input to the input shaft 122. The outlet end 124 of the output line 118 is preferably provided within the interior 128 of the collection chamber 126 above its lower side 130 so that a disposal line 132 leading from the collection chamber 126 at or near its lower side 130 can drain off water from the interior 128 of the collection chamber 126, while any gas bubbles exiting from the outlet end 124 of the output line 118 may float towards the upper side 134 of the collection chamber 126 for collection. Thus, by having the groundwater flow from the restrictor lines 110 enter the collection chamber 126 at a level above the height at which the disposal line 132 exits the collection chamber 126, gas bubbles may be collected without their disposal through the disposal line 132 along with excess groundwater.

When the pump 120 is actuated to achieve a sufficiently high flow rate, the aforementioned gas bubbles form in the restrictor lines 110. It is believed that this occurs owing to the following principles. For a bubble to form in water, the sum of partial pressures ($\Sigma P_i$) of volatile gas species ($N_2$, $O_2$, Ar, etc.) must be in excess of the ambient hydrostatic pressure PH:

$$\Sigma P_i = PN_2 + PO_2 + PAr + PH_2O + \ldots > PH$$

Thus, spontaneous formation of bubbles (ebullition) can be induced by decreasing the hydrostatic pressure on the right-hand side of the equation. In the apparatus 100, wherein the pump 120 is situated downstream from the restrictor lines 110, the suction from the pump 120 works on the fluid in the restrictor lines 110. The restrictor lines 110 offer relatively high resistance to this suction owing to fluid friction within the restrictor lines 110, which may be enhanced by making the flow areas of the restrictor lines 110 smaller and/or by making the restrictor lines 110 longer. Thus, the fluid within each of the restrictor lines 110 is subjected to a drop in hydrostatic pressure upstream from the inlet of the pump 120, causing bubble generation to occur in these areas. The theoretical basis for the invention's operation may be explained by the Darcy-Weisbach equation, which may be expressed as:

$$hf = \frac{f}{2g}\frac{V^2}{D}L = \frac{16}{\Pi^2}\frac{f}{2g}\frac{Q^2}{D^5}L$$

Where hf is the head loss in a fluid passage;
  f is the resistance coefficient;
  g is the gravitational constant;
  L is the length of the fluid passage;
  D is the diameter of the passage;
  V is the mean velocity of the fluid in the passage; and
  Q is the volumetric flow rate of the fluid in the passage.
Thus, it is seen that the head loss is dependent on (1) how small the diameter of the flow passage is; (2) how great the velocity/flow rate of the fluid is; and (3) how long the fluid passage is.

Bubble generation and gas collection can also be enhanced if additional or alternative measures are taken to enhance the pressure drop in the restrictor lines 110. Initially, the restrictor lines 110 can be provided with a lower combined flow area than the flow area of the intake line 102. If the flow area along a fluid passage is decreased, conservation of mass dictates that the fluid must necessarily undergo a velocity increase in the decreased flow area. Pressure will then decrease in the decreased flow area owing the velocity increase experienced by the fluid (with increased velocity resulting in a pressure decrease as per Bernoulli's equation). Similarly, it may be beneficial to provide the output line 118 with a lower flow area than the intake line 102, and also preferably lower than the combined flow area of the restrictor lines 110, to further enhance bubble generation upstream from the collection chamber 126. A decrease in hydrostatic pressure within the restrictor lines 110 may also be promoted where the restrictor lines 110 are situated at a greater height than the groundwater source 10, since fluid necessarily undergoes a decrease in hydrostatic pressure as it rises through a column.

It should be understood that more or less than two restrictor lines 120 may be used, with the foregoing design considerations being taken into account. More than one restrictor line 110 is generally preferred since this will offer more than one flow area wherein bubbles may be generated, thus potentially allowing an increase in the rate of gas collection within the collection chamber 126.

The pump 120, while depicted downstream from the restrictor lines 110, may be situated elsewhere within the fluid circuit (e.g., within the disposal line 132). While the pump 120 repressurizes the two-phase gas bubble/groundwater mixture when it is situated between the restrictor lines 110 and the gas collection chamber 126, it has been found that such repressurization is of sufficiently short duration that the gas bubbles do not significantly redissolve within the groundwater prior to entering the collection chamber 126, and thus the collected gas yield is not significantly diminished. The pump 120, if not self-priming, is easier to prime when it is situated nearer to the inlet end 104 of the intake line 102, but since the inlet end 104 may be submerged in a stream or pond, or inserted within a borehole, the versatility of the apparatus 100 may be diminished if the pump 120 is situated too near the inlet end 104.

The collection chamber 126 is then situated downstream from the restrictor lines 110 wherein the gas bubbles precipitate. Sufficient overhead space is provided in the collection chamber 126 that gas bubbles will buoyantly float to the upper side 134 of the collection chamber 126, allowing the gas bubbles to be harvested for analysis. Since gas partial pressures may be presumed to be proportional to gas mole fractions as per Dalton's Law, the partial pressures of individual gases within the collection chamber 126 may be determined, and used to quantify the gas content in the bulk fluid.

To harvest the gases collected at the upper side 134 of the collection chamber 126, the collection chamber 126 is preferably provided with a sampling port 136, and a valve 138 which selectably allows access to the interior 128 of the collection chamber 126. A sample collector 140 may then be provided which has a mouth 142 which is removably attachable to the sampling port 136, and which has an interior 144 with adjustable size. Thus, when the sample collector mouth 142 is fit on the sampling port 136, the valve 138 may be opened, and the sample collector interior 144 can be expanded to draw off the gases collected within the collection chamber 126 into the sample collector interior 144. Here the sample collector 140 is depicted as a syringe wherein its interior 144 is expanded when the plunger 146 is withdrawn, though other forms of sample collectors are possible. A valve 148 is also preferably provided on the sample collector 140 so that any gases withdrawn into its interior 144 may be sealed therein to allow transport of the gases to a gas chromatograph or other analysis device. A sample collector could instead take the form of a sample chamber which may be removably connected to the collection chamber 126 and selectively closed at its inlet, as with the syringe 140, but which does not have an interior with adjustable size. Instead, the ability to expel the collected gas from the interior of the sample chamber might be provided by having a separate second inlet through which a carrier gas or displacing fluid might be introduced to allow displacement of the collected gas from the sample collector's interior.

The apparatus 100 is preferably designed as a compact unit which may be readily carried into the field for gas sampling at remote locations, and thus it is useful to provide at least the intake line 102 and restrictor lines 110 in the form of flexible tubing which may be readily coiled and assembled/disassembled when desired. The collection chamber 126 is preferably rigid for ease of handling. The pump 120 (which will also generally be rigid) is preferably situated adjacent the collection chamber 126 so that all rigid components are adjacently situated for easier storage and handling, allowing the intake line 102 and restrictor lines 110 to simply be coiled about the rigid components for transport and uncoiled for use. It is preferable to form most or all of the various components of transparent materials (e.g., to form the intake line 102 and restrictor lines 110 of transparent tubing, and the collection chamber 126 of transparent materials) so that a user may monitor the apparatus 100 for fouling during its use, and so that bubble formation within the restrictor lines 110 and gas collection within the collection chamber 126 may be monitored.

Versions of the apparatus 100 have been tested using transparent nylon tubing (2.0 mm inner diameter) as the intake line 102; two 3-meter segments of nylon tubing (2.0 mm inner diameter) as the restrictor lines 110; an output line 118 formed of 0.8 m of the same nylon tubing (2.0 mm inner diameter); a self-priming Masterflex Model U 07024-21 tubing pump head (Cole-Parmer Instrument Co., Vernon Hills, Ill.) for the pump 120; and a standard laboratory counterflow trap (made of glass) for the collection chamber 126. When the pump 120 was driven at approximately 1000 rpm by a cordless drill (which is a particularly convenient and portable pump driver for field use), the pressure in the restrictor lines 120 upstream from the pump 120 decreased to an estimated 0.1 atm, and a groundwater throughput of approximately 340 ml/min was achieved. The output line 118 extended into the collection chamber 126 to provide approximately 5 cm of head space adjacent the upper side 134 of the collection chamber 126 wherein gases could collect.

An exemplary gas collection procedure is as follows. Before sample collection, the disposal line 132 is raised above the collection chamber 126 to establish a back pressure against which the pump 120 will work. About one liter of groundwater is then pumped with the sampling port valve 138 opened, forcing groundwater flow through both the sampling port valve 138 and the disposal line 132, cleaning the collection chamber 126 and displacing all gases therein. The sampling port valve 138 is then closed, leaving only water within the collection chamber 126. As water is pumped to the disposal line 132, gas collection occurs at the upper side 134 of the collection chamber 126. When sufficient gas has accumulated, pumping is stopped and the sampling port valve 138 and sample collector valve 148 are opened to allow collection of the gases into the gas-tight sample collector 140. If the disposal line 132 is raised so that its water level is held even with the water level at the upper side 134 of the collection chamber 126, the pressure within the collection chamber 126 and sample collector 140 are approximately the same as ambient atmospheric pressure during collection of gases into the sample collector 140.

When the foregoing arrangement is used with standard groundwater sources, approximately 5 to 8 ml of gas (at approximately atmospheric pressure) per liter of water may be collected at a pumping rate of about 340 ml/min. The total amount of gas collected depends on how long the sampling period lasts. Advantageously, so long as the groundwater supply is not limited, the invention allows collection of a sufficiently large volume of gas that trace gases, such as CFCs and $SF_6$, may be accumulated in sufficient amounts that their content and amount may be more accurately measured.

The collected gas can then be analyzed using a variety of known methods, with an exemplary analysis method proceeding as follows. Gas samples collected from groundwater were maintained in gas-tight 10 ml syringes until analysis. Water temperature and ambient barometric pressure were measured prior to extracting the gas. The total pressure, $P_T$, of dissolved gas was measured relative to laboratory barometric pressure $BP_{lab}$ using a total dissolved gas saturation monitor in percent saturation mode:

$$P_T = BP_{lab} \cdot \%SAT/100$$

The gas samples were then analyzed for general content to help define appropriate methods for subsequent gas analysis. $N_2$, Ar, $O_2$, $N_2O$, $CO_2$, and $H_2$ were detected using a pulse discharge detector (PDD) in the helium ionization mode (16), $SF_6$ was detected using a PDD in electron capture mode (17), and chlorofluorocarbons were detected using a $^{63}$Ni electron capture detector. Gas chromatography was then used to measure the mole fractions ($X_i$) of the detected gases ($N_2$, Ar, $O_2$, $N_2O$, $CO_2$, $CH_4$, $H_2$, CFC11, CFC12, CFC13 and $SF_6$). The chromatographic conditions for $N_2$, Ar, and $O_2$ were defined as in (13); for $N_2O$, $CH_4$ and $CO_2$, as defined in (3); for $SF_6$, as defined in (18); and for CFC11, CFC12, and CFC13, as defined in (8). Conditions were modified (e.g., substitution of He carrier gas) as necessary to accommodate use of a PDD. The samples, along with gas standards, were transferred from syringes to a sample loop on a six-port valve for injection onto the GC column. Six point calibration curves (mole fraction versus peak area) were performed by injection of gas dilutions prepared by mixing precisely measured aliquots of blank gases and standard gas. In load position, the sample loop was maintained at ambient lab temperature and pressure prior to injection.

After gas chromatography yielded mole fractions, the partial pressure $P_i$ of each gas in the water sample was calculated using the following relationship:

$$P_i = X_i \cdot P_T / F_{c,i}$$

Here the product $X_i \cdot P_T$ equals the partial pressure of the gas in the water sample, and $F_{c,i}$ is a gas specific fractionation coefficient which accounts for gas solubility and other factors:

$$F_{c,i} = X_{i,M}/X_{i,A}$$

where $X_{i,M}$ is the measured mole fraction of a reference sample of the gas in question when this gas is extracted from equilibrated water by use of the invention, and $X_{i,A}$ is the mole fraction of the same gas as measured from direct injection of a reference sample into a chromatograph. The fractionation coefficient is believed to enhance accuracy because the invention to some degree forcibly extracts gases from water, and owing to the solubility of each gas in water (among other factors), the amounts of the extracted gases might differ from those that would occur under equilibrium conditions (i.e., if the gases were allowed time to come to equilibrium in a headspace above water). It was found that for most gases, the variance of the fractionation coefficient $F_{c,i}$ from unity was negligible or small (i.e., differences between $X_{i,M}$ and $X_{i,A}$ are negligible or small). However, some gases had marked differences in extractability between the amounts recovered by the method of the invention and the amounts recovered at equilibrium. For example, $SF_6$ (which has low solubility in water) had a fractionation coefficient $F_{c,i}$ near 0.5. In contrast, CFC11 (higher solubility) had a fractionation coefficient $F_{i,c}$ near 1.2. However, the fractionation coefficients $F_{c,i}$ for different gases did not always correspond to their solubility, suggesting that the basis for deviation of fractionation coefficients $F_{c,i}$ from unity requires further investigation. Some experiments were performed to see whether fractionation coefficients $F_{c,i}$ varied with temperature, and while no variation was found for a selected group of gases, further testing to determine whether fractionation coefficients $F_{c,i}$ vary with temperature would be useful.

The individual gas concentrations determined by use of the invention were checked for accuracy versus results obtained by other methods and versus known concentrations in reference gas mixtures, and it was found that the invention allows accurate extraction of gases from groundwater and measurement of their concentrations. The measured gas concentrations compared favorably to concentrations measured by other methods, e.g., headspace equilibration, membrane electrode and Winkler titration methods (for $O_2$), etc.

Depending on the quality of the syringes or other sample collectors used, there may be limitations on the duration of sample integrity. Thus, samples are best analyzed as soon as possible after they are collected. However, because the invention reduces sample preparation in the lab, analysis speeds can effectively be increased, thereby reducing any backlog of specimens waiting to be tested and allowing newly-obtained samples to be analyzed sooner.

The apparatus 100 of the invention need not take the form of a portable apparatus, and may instead take the form of a semi-permanent or permanent installation if desired (e.g., near landfills or other sites where groundwater monitoring is useful). It is not necessary that the collected gases necessarily be analyzed; for example, where groundwater contamination is present, the invention might be used to decrease the pressure of the groundwater so that any volatile contaminants flash off into gas for collection, and the separated groundwater may be allowed to flow back to its source.

It is understood that preferred versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

Bibliography (1) Martin, G. E.; Snow, D. D.; Kim, E.; Spalding, R. F. *Ground Water*. 1995, 33, 781–785.
(2) Modica, E.; Buxton, H. T.; Plummer, L. N. *Water Resources Research*. 1998, 34, 2797–2810.
(3) McMahon, P. B.; Bruce, B. W.; Becker, M. F.; Pope, L. M.; Dennehy, K. F. *Environ. Sci. Technol*. 2000, 34, 4873–4877.
(4) Cole, J. J.; Caraco, N. F. *Environ. Sci. Technol*. 2001, 35, 991–996.
(5) Chapelle, F. H.; McMahon, P. B.; Dubrovsky, N. M.; Fujii, R. F.; Oaksford, F. T.; Vroblesky, D. A. *Water Resources Research*. 1995, 31, 359–371.
(6) Stute, M., Schlosser, P. Principles and applications of the noble gas paleothermometer. In Climate Change in Continental Isotopic Records; American Geophysical Union: Washington, DC, 1993; pp. 89–100.
(7) Busenberg, E.; Plummer, L. N. *Water Resources Research*. 2000, 36, 3011–3030.
(8) Busenberg, B.; Plummer, L. N. *Water Resources Research*. 1992, 28, 2257–2283.
(9) Heaton, T. H. E., Vogel, J. C. J. *Hydrology* 1981, 50, 201–216.
(10) Clark, J. F., Wanninkhof, R., Schlosser, P. and Simpson H. J. *Tellus* 1994, 46B, 274–285.
(11) Dixon, K. W., Bullister, J. L., Gammon, R. H., Stouffer, R. J. *Geophysical Research Letters* 1996 23 (15) 1957–1960.
(12) Baehr, A. L., Charles, E. G., Baker, R. J. 2001, *Water Resources Research* 2001, 37 (2), 223–233.
(13) http://water.usgs.gov/lab/dissolved-gas/sampling/index.html
(14) Beyerle, U.; Aeschbach-Hertig, W.; Imboden, D. M.; Baur, H.; Graf, T.; Kipfer, R. *Environ. Sci. Technol*. 2000, 34, 2042–2050.
(15) Chapelle, F. H.; Vroblesky, D. A.; Woodware, J. C.; Lovley, D. R. *Environ. Sci. Technol*. 1997, 31, 2873–2877
(16) Wentworth, W. E., Cai, H., Stearns, S. J. *Chromatography* 1994, A 688, 135–152.
(17) Wentworth, W. E., D'Sa, E. D., Cai, H.; Stearns, S. D. J. *Chromatographic Sci*. 1992, 30, 478–485.
(18) Wanninkhof, F.; Ledwell, J. R.; Watson, A. J. *J. Geophys. Res*. 1991, 96, 8733–8740.

What is claimed is:

1. An apparatus for collecting dissolved gases from groundwater comprising:
   a. an intake line having an inlet end and a downstream outlet end, the intake line having an intake line flow area defined therein;
   b. one or more restrictor lines, each extending between an inlet end and a downstream outlet end and each having a restrictor line flow area defined therein, wherein the inlet end of each restrictor line is in fluid communication with the intake line;
   c. a pump situated downstream from the restrictor lines;
   d. a gas collection chamber downstream from the restrictor lines, the gas collection chamber having an upper side, an opposing lower side, and an interior;
   e. a disposal line exiting the gas collection chamber.

2. The apparatus of claim 1 wherein any fluid flow from the outlet end of each restrictor line is received within the interior of the gas collection chamber above the height at which the disposal line exits the gas collection chamber.

3. The apparatus of claim 1 wherein the disposal line exits the gas collection chamber at or near the lower side of the gas collection chamber.

4. The apparatus of claim 1 further comprising a sampling port defined in the gas collection chamber.

5. The apparatus of claim 4 wherein the sampling port is situated at or near the upper side of the gas collection chamber.

6. The apparatus of claim 4 further comprising a sample collector which includes:
   a. an interior with adjustable size, and
   b. a mouth removably attachable to the sampling port,
whereby the mouth may be attached to the sampling port and the interior of the sample collector may be expanded to withdraw at least some of the contents of the gas collection chamber.

7. The apparatus of claim 1 wherein the restrictor line flow areas of all restrictor lines collectively define a total restrictor flow area which is less than the intake line flow area.

8. The apparatus of claim 1 wherein the pump is adapted for removable attachment to a separate driver, whereby a driver may be attached to the pump to actuate the pump.

9. The apparatus of claim 8 wherein the pump has a protruding shaft, and wherein a rotary input supplied to the shaft actuates the pump.

10. The apparatus of claim 1 wherein at least one of
   a. the intake line, and
   b. the restrictor lines,
are flexible.

11. The apparatus of claim 1 wherein at least one of
   a. the intake line,
   b. the restrictor lines, and
   c. the collection chamber,
are transparent.

12. An apparatus for collecting dissolved gases from groundwater comprising:
   a. an intake line having an inlet end and a downstream outlet end, the intake line having an intake line flow area defined therein;
   b. pumping means for supplying groundwater to the intake line;
   c. restrictor means located downstream from the intake line and receiving groundwater flowing therefrom, the restrictor means decreasing the pressure of the groundwater to a degree sufficient that at least a portion of any gases dissolved within the groundwater precipitate therefrom;
   d. gas collection means for collecting at least a portion of any precipitated gases;
   e. a disposal line leading from the gas collection means, whereby the groundwater from which the gases have been precipitated may be disposed from the gas collection means.

13. The apparatus of claim 12 wherein the restrictor means includes two or more restrictor lines, each extending between an inlet end and a downstream outlet end and each having a restrictor line flow area defined therein, wherein the inlet end of each restrictor line is downstream from the outlet end of the intake line.

14. The apparatus of claim 13 wherein the restrictor line flow areas of all restrictor lines collectively define a total restrictor flow area which is less than the intake line flow area.

15. The apparatus of claim 12 wherein the pumping means is located downstream from the restrictor means.

16. The apparatus of claim 12 wherein the gas collection means includes a gas collection chamber having an upper side, an opposing lower side, and an interior, and wherein the disposal line exits the gas collection chamber at or near the lower side of the gas collection chamber.

17. A process for collecting dissolved gases from groundwater comprising:
   a. supplying groundwater to an intake line having an inlet end and a downstream outlet end;
   b. directing the groundwater through a restrictor downstream from the inlet end of the intake line;
   c. decreasing the pressure of the groundwater within the restrictor to a degree sufficient that at least a portion of any gases dissolved within the groundwater precipitate therefrom;
   d. collecting at least a portion of any precipitated gases; and
   e. disposing of the groundwater from which the gases have been precipitated.

18. The process of claim 17 wherein the following steps are performed prior to supplying groundwater to the intake line:
   a. transporting the intake line in a folded state to a groundwater sampling site;
   b. unfolding the intake line at the groundwater sampling site; and
   c. placing the inlet end of the intake line into the groundwater to be supplied to the intake line.

19. The process of claim 18 wherein any precipitated gases are collected in a gas collection chamber, and wherein the gas collection chamber is transported to the groundwater sampling site with the intake line.

20. The process of claim 17 wherein the restrictor is provided by two or more restrictor lines.

* * * * *